United States Patent [19]

Bradshaw et al.

[11] Patent Number: 4,864,033

[45] Date of Patent: Sep. 5, 1989

[54] NOVEL LIQUID CRYSTALLINE COMPOUNDS AND POLYMERS

[75] Inventors: Jerald S. Bradshaw, Provo, Utah; Brian A. Jones, Marietta, Ohio; Karin E. Markides, Provo; Milton L. Lee, Pleasant Grove, both of Utah

[73] Assignee: Brigham Young University, Provo, Utah

[21] Appl. No.: 802,856

[22] Filed: Nov. 27, 1985

[51] Int. Cl.$^4$ .................. C07D 209/84; C07D 209/86
[52] U.S. Cl. .................................... 548/446; 549/43; 549/44; 585/825
[58] Field of Search .................... 548/446; 549/43, 44; 585/825

[56] References Cited

U.S. PATENT DOCUMENTS

| | | | |
|---|---|---|---|
| 2,622,087 | 12/1952 | DeBruigin | 548/446 |
| 2,777,889 | 1/1957 | Naumann | 548/446 X |
| 3,624,174 | 11/1971 | Sugerman | 548/446 X |
| 3,843,518 | 10/1974 | Magee et al. | 585/825 |
| 4,001,111 | 1/1977 | Geissler et al. | 585/825 |
| 4,069,142 | 1/1978 | Sauder et al. | 585/825 X |
| 4,584,120 | 4/1986 | Fujii et al. | 252/299.63 |

FOREIGN PATENT DOCUMENTS 2944591.8  7/1979  Fed. Rep. of Germany ...... 585/828

OTHER PUBLICATIONS

George M. Janini et al., "Synthesis and Properties of High Temperature Mesomorphic Polysiloxane (MEPSIL) Solvents. Amide, Ester and Schiff's Base Linked Systems", Makromol. Chem., Rapid Commun., vol. 6, pp. 57–63 (1985).

Qi-Feng Zhou et al., "Substituent Effects on the Liquid Crystalline Properties of Thermotropic Polyesters", Symposium on Polymeric Liquid Crystals—American Chemical Society Abstract, vol. 24, No. 2 (Aug. 1983).

A. Blumstein et al., "Linear Thermotropic Nematic Polymers; Odd–Even Effects in Polyesters and Copolyesters Containing a Substituted Azoxybenzene Moiety", Symposium on Polymeric Liquid Crystals—American Chemical Society Abstract, vol. 24, No. 2 (Aug. 1983).

L. Makaruk et al., "Preparation and Properties of Thermotropic Polyamidoesters", Symposium on Polymeric Liquid Crystals—American Chemical Society Abstract, vol. 24, No. 2 (Aug. 1983).

M. J. Seurin et al., "Liquid Crystalline Polymer Solutions and Mixtures", Symposium on Polymeric Liquid Crystals—American Chemical Society Abstract, vol. 24, No. 2 (Aug. 1983).

S. N. Bhadani et al., "Lyotropic and Thermotropic Liquid-Crystalline Phase Formation from Fractions of a Semiflexible Cellulose Polymer", Symposium on Polymeric Liquid Crystals—American Chemical Society Abstract, vol. 24, No. 2 (Aug. 1983).

(List continued on next page.)

Primary Examiner—Paul F. Shaver
Attorney, Agent, or Firm—Thorpe, North & Western

[57] ABSTRACT

The present invention relates to novel liquid crystalline compounds having the following formula:

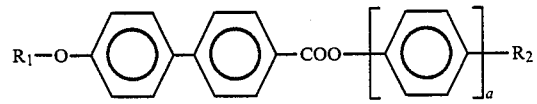

In the above formula, a is 1 or 2, or $R_1$ and $R_2$ may be virtually any chemical groups which will maintain the liquid crystalline properties of the resultant compound. The novel compounds of the present invention contain a biphenylcarboxylate ester moiety so as to define a new class of liquid crystalline compounds. The present invention further includes polymers made from the novel liquid crystalline compounds by attaching the compounds to a polymer backbone such as a polysiloxane backbone. Additionally, the present invention also contemplates methods for using such polymers as stationary phases in the chromatographic analysis of various chemical compounds, such as polycyclic aromatic hydrocarbons (PAH).

13 Claims, 4 Drawing Sheets

OTHER PUBLICATIONS

Penelope A. Patton et al., "Anisotropic Solutions of Methylol Cellulose", Symposium on Polymeric Liquid Crystals—American Chemical Society Abstract, vol. 24, No. 2 (Aug. 1983).

P. Navard et al., "Thermal Behavior of Mesomorphic Cellulose Derivative Solutions", Symposium on Polymeric Liquid Crystals—American Chemical Society Abstract, vol. 24, No. 2 (Aug. 1983).

B. Gallot et al., "Synthesis of Lyotropic Lipopeptides and Structural Study of Their Liquid Crystalline Phases", Symposium on Polymeric Liquid Crystals—American Chemical Society Abstract, vol. 24, No. 2 (Aug. 1983).

Charles L. McCormick et al., "Evidence for Lyotropic Mesophases of Cellulose in DMAc/LiCl Solutions", Symposium on Polymeric Liquid Crystals—American Chemical Society Abstract, vol. 24, No. 2 (Aug. 1983).

R. B. Blumstein et al., "NMR Investigation of Some Factors Influencing Nematic Ordering in a Linear Thermotropic Polyester, in Bulk and in Solution in Nematic PAA", Symposium on Polymeric Liquid Crystals-American Chemical Society Abstract, vol. 24, No. 2 (Aug. 1983).

Ya. S. Freidzon et al., "Cholesteric Copolymers with Side Mesogenic Groups", Symposium on Polymeric Liquid Crystals-American Chemical Society Abstract, vol. 24, No. 2 (Aug. 1983).

V. N. Tsvetkov et al., "Conformational Properties of Mesogenic Polymers in Solutions", Symposium on Polymeric Liquid Crystals—American Chemical Society Abstract, vol. 24, No. 2 (Aug. 1983).

D. Hoppner et al., "Analysis of Orientation Fluctuations in Liquid Crystals", Symposium on Polymeric Liquid Crystals—American Chemical Society Abstract, vol. 24, No. 2 (Aug. 1983).

X. Wang et al., "Rheo-Optical and X-Ray Studies of Thermotropic Liquid Crystalline Polymers", Symposium on Polymeric Liquid Crystals—American Chemical Society Abstract, vol. 24, No.2 (Aug. 1983).

John Blackwell et al., "X-Ray Studies of the Structures of Aromatic Liquid Crystalline Copolymers", Symposium on Polymeric Liquid Crystals—American Chemical Society Abstract, vol. 24, No. 2 (Aug. 1983).

Robin A. Chivers et al., "X-Ray Studies of the Structure of HBA/HNA Copolyesters", Symposium on Polymeric Liquid Crystals—American Chemical Society Abstract, vol. 24, No. 2 (Aug. 1983).

B. Wunderlich et al., "Do Condis Crystals Exist?", Symposium on Polymeric Liquid Crystals—American Chemical Society Abstract, vol. 24, No. 2 (Aug. 1983).

D. G. Baird et al., "Transient Shear Flow Behavior of Thermotropic Liquid Crystalline Copolyesters", Symposium on Polymeric Liquid Crystals—American Chemical Society Abstract, vol. 24, No. 2 (Aug. 1983).

S. Venkatraman et al., "Transient and Steady-State Rheology of Mesogenic Solutions of a Rodlike Polymer", Symposium on Polymeric Liquid Crystals—American Chemical Society Abstract, vol. 24, No. 2 (Aug. 1983).

T. Asada, "Rheo-Optical Studies on Strucutral Reformation of Nematic Liquid Crystals of Rod-Like Polymers after Cessation of Steady Flow", Symposium on Polymeric Liquid Crystals—American Chemical Society Abstract, vol. 24, No. 2 (Aug. 1983).

D. B. DuPre et al., "Determination of Elastic Constants in Weakly Birefringent Polymer Liquid Crystals", Symposium on Polymeric Liquid Crystals—American Chemical Society Abstract, vol. 24, No. 2 (Aug. 1983).

H. Ringsdorf et al., "Dielectric Relaxation of Liquid Crystalline Side Chain Polymers", Symposium on Polymeric Liquid Crystals—American Chemical Society Abstract, vol. 24, No. 2 (Aug. 1983).

R. V. Talroze et al., "Some Electro-Optical Phenomena in Comb-Like Polymeric Azomethynes", Symposium on Polymeric Liquid Crystals—American Chemical Society Abstract, vol. 24, No. 2 (Aug. 1983).

G. Huynh-ba, "Overview on Liquid Crystalline Polymers-Synthesis and Properties", Symposium on Liquid Crystals—American Chemical Society Abstract, vol. 24, No. 2 (Aug. 1983).

NOVEL LIQUID CRYSTALLINE COMPOUNDS AND POLYMERS

BACKGROUND

1. The Field of the Invention

The present invention relates to novel liquid crystalline compounds and polymers and methods employing such compounds and polymers as stationary phases in the gas, liquid, and supercritical fluid chromatographic separations and analyses of various substances such as polycyclic aromatic hydrocarbons.

2. The Prior Art

Liquid crystalline compounds and polymers are known for their utility as stationary phases in chromatography. Typically, in such liquid crystalline polymers, mesomorphic side chains of various chemical composition are attached to a polymer backbone. The liquid crystalline polymers are actually crystalline solids at low temperatures, but become "liquid" at higher temperatures, depending upon the specific mesomorphic side chains and polymer backbone employed.

Upon heating the solid crystalline compound, a smectic phase may be reached wherein the compound assumes a more liquid nature. Although in the liquid smectic phase the molecules of the compound are relatively ordered, this order is not as high as that in the crystalline phase. By increasing the temperature, the compound may then enter a nematic phase which is still liquid, but less ordered than the smectic phase. Finally, upon further increase in temperature, the compound may enter an isotropic phase wherein the compound is completely disordered with individual molecules positioned at complete random.

It should be noted that some liquid crystalline compounds and polymers have only a smectic phase or a nematic phase. Compounds that have neither a smectic phase or a nematic phase, however, are not liquid crystals.

Because of their respective degrees of high order and high disorder, the crystalline phase and isotropic phase of liquid crystalline polymers generally do not have utility in chromatographic separation. Thus, those skilled in the art have sought to develop liquid crystalline compounds and polymers having either smectic phases or nematic phases which are suitable for chromatography applications.

In capillary chromatography, achieving maximum separation of components, which is extremely important for successful identification of those components, and achieving maximum resolution of the chromatographic peaks depends on at least two important factors: (1) selectivity and (2) efficiency. Simply stated, selectivity has reference to the distance between the peaks in the resultant chromatogram, whereas efficiency relates to minimizing the width of the peaks. Thus, both selectivity and efficiency affect the resultant resolution and separation of the peaks in the resultant chromatogram. Unfortunately, in the prior art, it has been difficult to maximize both selectivity and efficiency using liquid crystalline compounds and polymers as stationary phases.

In a typical chromatography apparatus, it is desirable to have a stationary phase which is operable over a temperature range from about ambient temperature to about 300°–350° C. Such a temperature range allows gas-liquid chromatography programming to start at ambient temperature and go to higher temperatures as needed to separate the particular chemical components involved. Since the materials from which the gas-liquid chromatographic column and oven are manufactured dictate the limits of this temperature range, it is extremely important that the stationary phase used inside the column also have a versatile temperature range of operation.

The smectic phases of prior art liquid crystalline polymers typically cover much narrower temperature ranges than nematic phases. Thus, the prior art has particularly emphasized the use of liquid crystalline polymers having workable nematic phases. Further in this regard, it should be noted that nematic phases of liquid crystalline polymers usually exhibit better efficiency than smectic phases. However, smectic phases typically exhibit much better selectivity than nematic phases.

Thus, the choice faced in the prior art has been one of selectivity versus efficiency, both of which are needed for good separation results. As mentioned above, the prior art has focused primarily around nematic phase liquid crystalline polymers. In using the nematic phase, the requisite efficiency and temperature range can be obtained at the sacrifice of selectivity. On the other hand, the poor efficiency and narrow temperature ranges of the smectic phases have virtually prohibited usage of the prior art smectic phases in chromatography applications.

Thus, it will be recognized, that what is needed in the art are liquid crystalline compounds and polymers which have good selectivity, good efficiency, and can be used over a wide temperature range so as to provide practical and useful stationary phases in chromatography. Such liquid crystalline compounds and polymers are disclosed and claimed herein.

The prior art has also found that liquid-crystalline stationary phases provide improved capillary gas-liquid chromatography separations of some isomeric species, including some polycyclic aromatic hydrocarbons (PAH), that are difficult or impossible to resolve by other traditional chromatographic techniques. Polycyclic aromatic hydrocarbons are widespread environmental pollutants produced, for example, by the incomplete combustion of organic matter. Members of or derivatives of the PAH class of compounds represent the largest class of proven chemical carcinogens.

The carcinogenic properties of PAH compounds are frequently isomer specific. Thus, it would be highly useful in analyzing the levels of these pollutants to be able to separate PAH into separate isomeric components, and attempts have been made in the prior art to use capillary gas-liquid chromatography to separate such structurally related isomers.

Unfortunately, the liquid crystalline polymers of the prior art have not provided completely satisfactory results in separating PAH. Hence, it would be another advancement in the art to provide liquid crystalline compounds and polymers which could be used as stationary phases in chromatography to satisfactorily separate PAH into separate isomeric components. Such liquid crystalline compounds and polymers are also disclosed and claimed herein.

BRIEF SUMMARY AND OBJECTS OF THE INVENTION

The present invention relates to liquid crystalline compounds having the following general formula:

FORMULA 1

In the above Formula 1, a is 1 or 2; $R_1$ is hydrogen, alkyl, alkenyl, aryl, arylalkyl, arylalkenyl, or substitutions thereof, with $R_1$ having from about 0 to about 22 carbons in the main carbon chain; and $R_2$ is hydrogen, alkyl, alkoxy, carboxy alkyl, aryl, arylalkyl, arylalkoxy, carboxy arylalkoxy, hydroxy, hydroxy alkyl, cyano, cyano alkyl, amino, amino alkyl, amido, amido alkyl, or substitutions thereof, with $R_2$ having from about 0 to about 20 carbons in the main carbon chain.

The present invention also relates to polymers comprising, for example, a polysiloxane backbone to which are attached mesomorphic side chains formulated in accordance with Formula 1. Such polymers thus have the following general formula:

FORMULA 2

In the above Formula 2, a and d are integers from about 0 to about 22; b and e are either 1 or 2; c and f are integers from about 0 to about 10; g is an integer from about 1 to about 200; $R_1$ and $R_2$ are selected from the group consisting of hydrogen, alkyl, alkoxy, carboxy alkyl, aryl, arylalkyl, arylalkoxy, carboxy arylalkoxy, hydroxy, hydroxy alkyl, cyano, cyano alkyl, amino, amino alkyl, amido, amido alkyl, and substitutions thereof, with $R_1$ and $R_2$ each having from about 0 to about 20 carbons in the main carbon chain; $R_3$ and $R_{10}$ are selected from the group consisting of hydrogen, lower alkyl, lower aryl, lower arylalkyl, lower silyl alkyl, and substitutions thereof; and $R_4$, $R_5$, $R_6$, $R_7$, $R_8$, and $R_9$ are hydrogen, lower alkyl, lower aryl, lower arylalkyl, other mesomorphic side chains formulated in accordance with Formula 1 above, or substitutions of any of the foregoing.

As noted in the above Formulas 1 and 2, the liquid crystalline compounds and polymers of the present invention are characterized by an ether-biphenyl-ester-phenyl or an ether-biphenyl-ester-biphenyl moiety. The positioning of the biphenyl group between the ether group and the ester group provides a new class of liquid crystalline compounds and polymers which has superior characteristics to prior art liquid crystalline compounds.

In this regard, it has been discovered that the polymers of Formula 2 exhibit good selectivity, good efficiency, and are operable within a wide temperature range in the smectic phases of the polymers. Thus, surprisingly, the liquid crystalline compounds and polymers of the present invention exhibit smectic phases which achieve better separation of various chemical components than the prior art liquid crystalline compounds and polymers. In particular, the liquid crystalline polymers of the present invention have shown superior utility in the chromatographic separation of PAH isomers.

Thus, the present invention further contemplates methods for employing the liquid crystalline polymers as stationary phases in the chromatographic separation of various chemical compounds such as PAH.

It is, therefore, an object of the present invention to provide novel liquid crystalline compounds and polymers.

Another object of the present invention is to provide novel liquid crystalline compounds and polymers which contain a biphenylcarboxylate ester moiety.

A further object of the present invention is to provide liquid crystalline polymers having smectic phases which exhibit good selectivity and good efficiency over a wide temperature range.

Still another object of the present invention is to provide liquid crystalline compounds and polymers which may be employed as stationary phases in the chromatographic separation of compounds such as difficult-to-separate isomeric PAH, and thereby provide superior separation than achieved in the prior art.

Yet another object of the present invention is to provide superior methods for separating various chemical components from a mixture of chemical components using gas-liquid chromatography.

These and other objects and features of the present invention will become more fully apparent from the following description and appended claims, taken in conjunction with the accompanying drawings.

DETAILED DESCRIPTION OF THE PREFERRED EMBODIMENTS

The present invention relates to novel liquid crystalline compounds, and novel liquid crystalline polymers which exhibit exceptional utility as stationary phases in the chromatographic separation of various chemical substances. The novel liquid crystalline compounds of the present invention have the following general formula:

FORMULA 1

In Formula 1 above, a is 1 or 2, with a being 1 in the most presently preferred embodiment. Although it is possible for a to be integers larger than 2, it has been found that the chromatographic utility of the compound tends to disappear when the value of a is increased much greater than 2.

Further, $R_1$ in Formula 1 above may be virtually any group which will maintain the liquid crystalline nature of the compound. For example, $R_1$ may be represented by hydrogen, an alkyl group, an alkenyl group, an aryl group, an arylalkyl group, an arylalkenyl group, or substitutions thereof. In one presently preferred embodiment of the present invention, $R_1$ is an alkenyl group having a terminal carbon-to-carbon double bond so as to facilitate linkage of the liquid crystalline compounds to a polymer backbone and thereby form a liquid crystalline polymer as will be discussed in more detail hereinafter.

Hence, in one presently preferred embodiment of the present invention, $R_1$ in Formula 1 is represented by: $CH_2=CH(CH_2)_b-$. In this alkenyl group, b is preferably an integer from about 0 to about 20. The result is an $R_1$ group having from about 0 to about 22 carbons in the main carbon chain. Although carbon chain lengths greater than this might be used, it has been found that the chromatographic utility of the resultant compounds tends to be lost when larger carbon chain lengths are used of Formula 1. The most presently preferred values for b in $R_1$ of Formula 1 are 1, 3, and 8.

Further in Formula 1 above, $R_2$ may also be represented by virtually any group which will maintain the liquid crystalline properties of the resultant compound. For example, $R_2$ may be represented by hydrogen, an alkyl group, an alkoxy group, a carboxy alkyl group, an aryl group, an arylalkyl group, an arylalkoxy group, a carboxy arylalkoxy group, a hydroxy group, a hydroxy alkyl group, a cyano group, a cyano alkyl group, an amino group, an amino alkyl group, an amido group, an amido alkyl group, or substitutions thereof. Again, in order to maintain the chromatographic utility of the resultant compound, it has been presently found preferable to maintain the main carbon chain of $R_2$ at a length of 20 carbons or less. As with $R_1$, although main carbon chain lengths greater than this are possible for $R_2$, it has been found that the chromatographic utility of the compound tends to disappear with such increasing chain lengths.

In four different presently preferred embodiments, $R_2$ is represented by an alkoxy group, a carboxy alkyl group, a carboxy arylalkoxy group, and a cyano group, respectively. For example, in such preferred embodiments, $R_2$ may be $-OCH_3$, $-COOCH_2CH(CH_3)CH_2CH_3$, $-COO(C_6H_4)OCH_3$, or $-CN$. However, many other chemical groups may also be used to produce compounds with liquid crystalline properties which are within the scope of the present invention. Thus, the chemical groups set forth for $R_2$ hereinabove are merely illustrative, and should not be considered comprehensive.

Further, it will be recognized that substitutions of any of the foregoing chemical groups for $R_1$ and $R_2$ will be within the scope of the present invention. By way of example only, substituting a halogen in one of these chemical groups for a hydrogen would be considered to be within the scope of the present invention. Thus, all well-known chemical substitutions or derivatives of the compounds of Formula 1 are to be considered within the scope of the present invention where the liquid crystalline properties are preserved.

One presently preferred procedure for preparing compounds in accordance with Formula 1 is given in Procedure I below.

Procedure I

In this procedure, an appropriate alkenyl halide (or alkenyl tosylate) is first reacted with 4-(4-hydroxyphenyl) benzoic acid in a one to one molar ratio, in accordance with Equation 1 below. In Equation 1, the alkenyl halide and [4-(4-hydroxy)phenyl] benzoic acid react to form an alkenyloxybiphenylcarboxylic acid. As will be appreciated, the value of a in Equation 1 below will depend upon the specific compound to be made.

EQUATION 1

In order to achieve the reaction of Equation 1, the 4-(4-hydroxyphenyl) benzoic acid is dissolved into solution at room temperature with a strong basic solution such as two equivalents of potassium hydroxide (KOH) or sodium hydroxide (NaOH) in an appropriate solvent such as ethanol. Next, the alkenyl halide (or alkenyl tosylate) is then dripped, for example, via an addition funnel, into the 4-(4-hydroxyphenyl) benzoic acid solution over a one to three hour period of time, while refluxing the solution under a condenser at a temperature corresponding to the reflux temperature of the mixture. If the alkenyl halide (or alkenyl tosylate) is not a liquid at room temperature, the alkenyl halide (or alkenyl tosylate) may be dissolved in an appropriate solvent such as ethanol before dripping, or the solid itself may be slowly added to the refluxing mixture. Completion of the reaction may require refluxing of the mixture for a period of about six to twenty-four hours.

The preferred alkenyl halides employed in this procedure include those wherein X in Equation 1 is represented by bromine (Br) or iodine (I). It has been found that these alkenyl bromides and alkenyl iodides are generally more reactive than their corresponding alkenyl chlorides, and are thus usually preferable. Further, it has been discovered that the rate of reaction in Equation 1 may be increased by adding some sodium iodide (NaI), for example about 0.1 molar equivalents, to the refluxing mixture. If desired, the reaction medium can be tested through standard thin layer chromatographic tests in order to determine the remaining quantities of reactants and the presence of product.

The resultant alkenyloxybiphenylcarboxylic acid is cooled to about 0° C. and is isolated from the refluxed solution by acidifying the solution with a suitable acid such as hydrochloric acid (HCl) or sulfuric acid ($H_2SO_4$) to a pH of about 2-3. The mixture is kept cold during the acidification process by adding ice as needed. The salts which are by-products of the reaction of Equation 1 will then dissolve into the water, while the alkenyloxybiphenylcarboxylic acid precipitates out of the water as a solid. The precipitate is then vacuum filtered from the water and the solid filtrate is washed with additional water in order to maximize the removal of the unwanted salt by-products from the filtrate. The alkenyloxybiphenylcarboxylic acid filtrate may then be purified by dissolving it into an appropriate heated solvent such as acetic acid or ethanol, and then cooling the solution to achieve recrystallization.

The next step in Procedure I is to react the purified alkenyloxybiphenylcarboxylic acid with thionyl chloride ($SOCl_2$) in order to produce the corresponding alkenyloxybiphenylcarboxylic acid chloride as shown in Equation 2 below.

EQUATION 2

To achieve the reaction of Equation 2, the alkenyloxybiphenylcarboxylic acid is placed in an appropriate solvent such as toluene or benzene with an excess of thionyl chloride, and the reaction mixture is stirred at room temperature for a period of about five hours until a clear solution remains. If desired, a small amount (for example, one drop) of dimethylformamide may be added to the reaction mixture so as to catalyze the reaction. The acid chloride product forms as a solid, with the by-products being released as gases. After the reaction is completed, the solvent is removed by evaporation under reduced pressure. Excess thionyl chloride is removed by adding repetitive 10–15 ml aliquots of benzene and removing the benzene-thionyl chloride azeotrope under vacuum. The acid chloride product may then be purified by recrystallization if desired, but this has generally not been found to be necessary.

In the final reaction step of Procedure I, the acid chloride (whether crude or purified) is reacted with an appropriate phenol in an esterification reaction as shown in Equation 3 below.

EQUATION 3

As will be appreciated, the R group in Equation 3 will vary according to the end product desired. For example, where the ester group of the final product is to be bordered by biphenyl groups on both sides, R will necessarily contain a phenyl moiety. If, however, a biphenyl-ester-single phenyl sequence is desired in the final product, R will not contain a phenyl moiety.

In order to achieve the reaction of Equation 3, the acid chloride is first dissolved at room temperature in an appropriate solvent such as methylene chloride. The resulting acid chloride solution is then slowly added to a cold solution (having a temperature within the range of about −10° C. to about +10° C.) of an equimolar amount of the appropriate phenol and an excess amount of triethylamine, both also in methylene chloride. The combined solution is then allowed to stand for a period of about two hours, and the solvent and excess triethylamine are removed by heating the mixture over a boiling water bath. The solid product thus obtained is a liquid crystalline compound within the scope of Formula 1 of the present invention.

This product may be purified by dissolving the product in an appropriate solvent such as methylene chloride and filtering the solution through silica gel. The silica gel is then washed with additional methylene chloride. Finally, the filtrate and washings are combined, and the solvents are removed by evaporation under reduced pressure to give a purified product representing a compound within the scope of Formula 1 above.

The following examples are given to illustrate various compounds which have been made or may be made in accordance with Formula 1 of the present invention. These examples are given by way of example only, and it is to be understood that the following examples are not comprehensive of the many different compounds which can be made in accordance with the present invention.

EXAMPLE 1

In this example, a liquid crystalline compound within the scope of the present invention was made wherein a=1, $R_1=CH_2=CH(CH_2)$—, and $R_2=-OCH_3$ in Formula 1. This compound, 4-methoxyphenyl 4-[4-(allyloxy)phenyl]benzoate, was made in accordance with the following procedure.

First, a small quantity of 4-[4-(allyloxy)phenyl]benzoic acid was prepared. In this regard, about 10 grams (0.047 mol) of 4-(4-hydroxyphenyl)benzoic acid, about 6 grams of potassium hydroxide (KOH), and about 0.1 grams of sodium iodide (NaI) were added to about 200 milliliters (ml) of ethanol ($C_2H_5OH$) at room temperature, and the resulting solution was heated to reflux temperature, i.e., about 78° C. Next, about 6.0 grams (0.049 mol) of allyl bromide were slowly added (dropwise from an addition funnel) to the solution over a period of about 2 hours, and the solution was refluxed over night under a condenser. The solution was then cooled to a temperature of about 10° C. using ice, poured into about 400 ml of ice water, and then acidified with concentrated hydrochloric acid (HCl) to a pH of about 2-3. The solid carboxylic acid product precipitated out of the water and was removed by vacuum filtration. The solid carboxylic acid filtrate was then washed with two 200 ml portions of water. The resultant 4-[4-(allyloxy)phenyl]benzoic acid product was then recrystallized from acetic acid to purify the product.

In the next step of Example 1, about 7.1 grams (28 mmol) of the 4-[4-(allyloxy)phenyl]benzoic acid product were placed in about 15 ml of benzene solvent, together with an excess (about 7.4 grams) of thionyl chloride ($SOCl_2$) and three drops of dimethylformamide, and this reaction mixture was stirred at room temperature for a period of about one-half hour until a clear solution remained. The acid chloride product formed as a solid, with the by-products being released as gases. After about 1 hour when the reaction was completed, the solvents were removed by evaporation under reduced pressure.

The crude acid chloride product was dissolved in about 25 ml of methylene chloride (tetrahydrofuran may also be used) at room temperature. The resulting acid chloride solution was then slowly added to a cold solution (having a temperature of about 10° C.) comprising about 1.7 grams of 4-methoxyphenol and about 1.5 grams of triethylamine in about 150 ml of methylene chloride. The combined solution was then stirred for a period of about 4 hours, after which time the solvent and excess triethylamine were removed by heating the mixture over a boiling water bath. As verified by infrared (IR) spectra and nuclear magnetic resonance (NMR) spectra, the resultant solid was 4-methoxyphenyl 4-[4-(allyloxy)phenyl]benzoate.

This product was then purified by dissolving the product in about 100 ml of methylene chloride and filtering the resultant solution through about 50 ml of silica gel. The silica gel was then washed with an additional 100 ml of methylene chloride. Finally, the filtrate and washings were combined, and the solvents were removed by evaporation under reduced pressure to yield the purified product.

The product of this example was recrystallized from methylene chloride and ethanol (in about a one-to-one volumetric ratio) to give white crystals (m.p. 139°-140° C.).

Except where otherwise indicated, in this and all other examples set forth herein, all chemicals were purchased from the Aldrich Chemical Company, Milwaukee, Wisconsin, except the 4-(4-hydroxyphenyl)-benzoic acid which was prepared according to the well-known four-step procedure of G. W. Gray et al. found, for example, at G. W. Gray et al., "J. Chem. Soc., 1412 (1955), which article is incorporated herein by reference.

EXAMPLE 2

In this example, a liquid crystalline compound within the scope of the present invention was made wherein $a=1$, $R_1=CH_2=CH(CH_2)-$, and $R_2=-COOCH_2CH(CH_3)CH_2CH_3$ in Formula 1. This compound, (S)-4-[(2-methyl-1-butoxy)carbonyl]phenyl 4-[4-(allyloxy)phenyl]benzoate, was made in accordance with the procedure of Example 1 with the following exceptions.

About 3.0 grams (12 mmol) of 4-[4-(allyloxy)phenyl]-benzoic acid were used in Example 2 instead of the 7.1 grams of this compound used in Example 1. Additionally, in Example 2, about 2.3 grams (12 mmol) of (S)-2-methyl-1-butyl 4-hydroxybenzoate were used in lieu of the 4-methoxyphenol used in Example 1. Methanol instead of ethanol and methylene chloride was used to recrystallize the product of this example.

The (S)-2-methyl-1-butyl 4-hydroxybenzoate used in Example 2, as well as in all other examples requiring this compound, was made according to the well-known procedure of Finkelmann and Rehage, set forth, for example, at H. Finkelmann et al., Makromol, Chem., Rapid Commun. 3, 859 (1982), which article is incorporated herein by reference. In particular, about 4.9 grams (0.036 mol) of 4-hydroxybenzoic acid and about 8.1 grams (0.092 mol) of (S)-2-methyl-1-butanol were mixed with 0.18 ml of sulfuric acid in 5.4 ml of benzene. This mixture was refluxed for about 16 hours until the acid dissolved. The resulting solution was then added to about 100 ml of ether, and was subsequently extracted with about 50 ml of aqueous sodium bicarbonate. The dried ether layer was evaporated to give about 6.5 grams (93%) of the ester product.

EXAMPLE 3

In this example, a liquid crystalline compound within the scope of the present invention was made wherein $a=1$, $R_1=CH_2=CH(CH_2)-$, and $R_2=CN$ in Formula 1. This compound, 4-cyanophenyl 4-[4-(allyloxy)-phenyl]benzoate, was made in accordance with the procedure of Example 1 with the following exceptions.

About 1.78 grams (7 mmol) of 4-[4-(allyloxy)phenyl]-benzoic acid were used in Example 3 instead of the 7.1 grams of this compound used in Example 1. Additionally, in Example 2, about 0.88 grams (7 mmol) of 4-cyanophenol were used in lieu of the 4-methoxyphenol used in Example 1.

The product of Example 3 was dissolved in about 40 ml of methylene chloride and about 50 ml of methanol were added. The methylene chloride was distilled off and the mixture was cooled to about 10° C. and filtered to give about 2.2 grams of a slightly yellow solid. This solid was dissolved in about 15 ml of boiling toluene. Upon cooling to about 10° C., the cold toluene solution yielded about 1.39 grams of white crystals which were filtered and dried.

EXAMPLE 4

In this example, a liquid crystalline compound within the scope of the present invention was made wherein $a=1$, $R_1=CH_2=CH(CH_2)-$, and $R_2=-COO(C_6H_4)OCH_3$ in Formula 1. This compound, 4-(4-methoxyphenoxycarbonyl)phenyl 4-[4-(allyloxy)phenyl]benzoate, was made in accordance with the procedure of Example 1 with the following exceptions.

About 2.54 grams (10 mmol) of 4-[4-(allyloxy)-phenyl]-benzoic acid were used in Example 4 instead of the 7.1 grams of this compound used in Example 1. Additionally, in Example 4, about 2.44 grams (10 mmol) of 4'-methoxyphenyl 4-hydroxybenzoate were used in lieu of the 4-methoxyphenol used in Example 1. About 110 ml of methanol instead of ethanol and methylene chloride were used to recrystallize the product of this example.

The 4-methoxyphenyl 4-hydroxybenzoate was prepared by the procedure of H. J. Deutsher et al., J. Prakt. Chem. 321, 47 (1979) as follows. A mixture of about 4.9 grams (36 mmol) of 4-hydroxybenzoic acid, about 4.96 grams (40 mmol) of 4-methoxyphenyl, about 10 drops of sulfuric acid, and about 20 ml of benzene were refluxed for about 6 days. Water was then removed with a Dean Stark trap. The reaction was monitored by thin layer chromatography, and when the 4-hydroxybenzoic acid was reacted, the solid product was filtered from the mixture. The crude product was then dissolved in about 250 ml of diethylether and was washed with saturated aqueous sodium bicarbonate and dried over anhydrous magnesium sulfate. Subsequently about 150 ml of ether was slowly distilled while 100 ml of hexane was added to give about 7.58 grams of white crystals (m.p. 190°–193° C.).

EXAMPLE 5

In this example, a liquid crystalline compound within the scope of the present invention was made wherein a=2, $R_1$=CH$_2$=CH(CH$_2$)—, and $R_2$=—OCH$_3$ in Formula 1. This compound, 4'-methoxybiphenyl-4-yl 4-[4-(allyloxy)phenyl]benzoate, was made in accordance with the procedure of Example 1 with the following exceptions.

About 4.0 grams (16 mmol) of 4-[4-(allyloxy)phenyl]benzoic acid were used in Example 5 instead of the 7.1 grams of this compound used in Example 1. Additionally, in Example 5, about 3.1 grams (16 mmol) of 4-(4-methoxyphenyl)phenol were used in lieu of the 4-methoxyphenol used in Example 1. Toluene instead of ethanol and methylene chloride was used to recrystallize the product of this example to give white flakes.

EXAMPLE 6

In this example, a liquid crystalline compound within the scope of the present invention was made wherein a=2, $R_1$=CH$_2$=CH(CH$_2$)—, and $R_2$=—COOCH$_2$CH(CH$_3$)CH$_2$CH$_3$ in Formula 1. This compound, (S)-4'-[(2-methyl-1-butoxy)carbonyl]-biphenyl-4-yl 4-[4-(allyloxy)phenyl]benzoate, was made in accordance with the procedure of Example 1 with the following exceptions.

About 3 grams (11.8 mmol) of 4-[4-(allyloxy)phenyl]benzoic acid were used in Example 6 instead of the 7.1 grams of this compound used in Example 1. Additionally, in Example 6, about 3.4 grams (11.8 mmol) of (S)-2-methyl-1-butyl 4-(4-hydroxyphenyl)benzoate were used in lieu of the 4-methoxyphenol used in Example 1. Ethanol was used to recrystallize the product of this example.

The (S)-2-methyl-1-butyl 4-(4-hydroxyphenyl)benzoate used in Example 6, as well as in all other examples employing this compound, was prepared as follows. About 8.1 grams (37.8 mmol) of 4-(4-hydroxyphenyl)benzoic acid, about 10 grams (113 mmol) of (S)-2-methyl-1-butanol, about 0.18 grams of sulfuric acid, and about 8 ml of benzene were mixed together and refluxed through a water separator for a period of about two days. After this period of time, about 100 ml of ether was added to the solution, and the solution was extracted twice with 10 ml portions of 5% aqueous sodium bicarbonate. The organic phase of the extraction was dried over anhydrous sodium sulfate, the ether was removed by evaporation, and the product was crystallized first from heptane and then from methanol to give white needles.

EXAMPLE 7

In this example, a liquid crystalline compound within the scope of the present invention was made wherein a=1, $R_1$=CH$_2$=CH(CH$_2$)$_3$—, and $R_2$=—OCH$_3$ in Formula 1. This compound, 4-methoxyphenyl 4-[4-(4-pentenyloxy)phenyl]benzoate, was made in accordance with the procedure of Example 1 with the following exceptions.

About 3 grams (10.6 mmol) of 4-[4-(4-pentenyloxy)phenyl]benzoic acid were used in Example 7 instead of the 7.1 grams of 4-[4-(allyloxy)phenyl]benzoic acid used in Example 1. Additionally, in Example 7, about 1.32 grams (10.6 mmol) of 4-methoxyphenol were used in Example 7 instead of the 3.4 grams of this compound used in Example 1. Methanol instead of ethanol and methylene chloride was used to recrystallize the product of this example.

The 4-[4-(4-pentenyloxy)phenyl]benzoic acid used in Example 7, as well as in all other examples requiring this compound, was made in accordance with the procedure for making 4-[4-(allyloxy)phenyl]benzoic acid set forth in Example 1, with the following exceptions. About 21.4 grams (0.10 mol) of 4-(4-hydroxyphenyl)benzoic acid were used in Example 7 instead of the 10 grams of this compound used in Example 1. Additionally, in Example 7, about 16 grams (0.11 mol) of 5-bromo-1-pentene were used in lieu of the allyl bromide used in Example 1. The resultant 4-[4-(4-pentenyloxy)phenyl]benzoic acid product was recrystallized from ethanol to give white crystals.

EXAMPLE 8

In this example, a liquid crystalline compound within the scope of the present invention was made wherein a=1, $R_1$=CH$_2$=CH(CH$_2$)$_3$—, and $R_2$=—COOCH$_2$CH(CH$_3$)CH$_2$CH$_3$ in Formula 1. This compound, (S)-4-[(2-methyl-1-butoxy)carbonyl]phenyl 4-[4-(4-pentenyloxy)phenyl]benzoate, was made in accordance with the procedure of Example 1 with the following exceptions.

About 3 grams (11 mmol) of 4-[4-(4-pentenyloxy)phenyl]benzoic acid were used in Example 8 instead of the 7.1 grams of 4-[4-(allyloxy)phenyl]benzoic acid used in Example 1. Additionally, in Example 8, about 2.1 grams (11 mmol) of (S)-2-methyl-1-butyl 4-hydroxybenzoate were used in lieu of the 4-methoxyphenol used in Example 1. Ethanol was used to recrystallize the product of this example.

EXAMPLE 9

In this example, a liquid crystalline compound within the scope of the present invention may be made wherein a=2, $R_1$=CH$_2$=CH(CH$_2$)$_3$—, and $R_2$=—OCH$_3$ in Formula 1. This compound, 4'-methoxybiphenyl-4-yl 4-[4-(pentenyloxy)phenyl]benzoate, may be made in accordance with the procedure of Example 1 with the following exceptions.

About 4.2 grams (16 mmol) of 4-[4-(4-pentenyloxy)phenyl]benzoic acid are used in Example 9 instead of the 7.1 grams of 4-[4-(allyloxy)phenyl]benzoic acid used in Example 1. Additionally, in Example 9, about 3.1 grams (16 mmol) of 4-(4-methoxyphenyl)phenol are used in lieu of the 4-methoxyphenol used in Example 1. Ethanol may be used to recrystallize the product of this example.

EXAMPLE 10

In this example, a liquid crystalline compound within the scope of the present invention was made wherein a=2, $R_1$=CH$_2$=CH(CH$_2$)$_3$—, and $R_2$=—COOCH$_2$CH(CH$_3$)CH$_2$CH$_3$ in Formula 1. This compound, (S)-4'-[(2-methyl-1-butoxy)carbonyl]biphenyl4-yl 4-[4-(4-pentenyloxy)phenyl]benzoate, was made in accordance with the procedure of Example 1 with the following exceptions.

About 3 grams (11 mmol) of 4-[4-(4-pentenyloxy)phenyl]benzoic acid were used in Example 10 instead of the 7.1 grams of 4-[4-(allyloxy)phenyl]benzoic acid used in Example 1. Additionally, in Example 10, about 3 grams (11 mmol) of (S)-2-methyl-1-butyl 4-(4-hydroxyphenyl)benzoate were used in lieu of the 4-methoxyphenol used in Example 1. Ethanol was used to recrystallize the product of this example.

EXAMPLE 11

In this example, a liquid crystalline compound within the scope of the present invention was made wherein a=1, $R_1$=CH$_2$=CH(CH$_2$)$_8$—, and $R_2$=—OCH$_3$ in Formula 1. This compound, 4-methoxyphenyl 4-[4-(9'-decenyloxy)phenyl]benzoate, was made in accordance with the procedure of Example 1 with the following exceptions.

About 2.91 grams (8.27 mmol) of 4-[4-(9'-decenyloxy)phenyl]benzoic acid were used in Example 11 instead of the 7.1 grams of 4-[4-(allyloxy)phenyl]benzoic acid used in Example 1. Additionally, in Example 11, about 1.03 grams (8.27 mmol) of 4-methoxyphenol were used instead of the 3.4 grams of this compound used in Example 1. Methylene chloride and methanol were used to recrystallize the product of this example.

The 4-[4-(9'-decenyloxy)phenyl]benzoic acid used in Example 11, as well as in all other examples requiring this compound, was made according to the following procedure. About 0.014 mol of 4-(4-hydroxyphenyl)-benzoic acid was dissolved in a hot solution of potassium hydroxide (about 0.028 mol KOH) in about 370 ml of 90% ethanol. About 0.014 mol of 10-bromo-1-decene (made from 9-decen-1-ol and phosphorous tribromide) was added to the mixture, and the mixture was refluxed for about 16 hours. Another potassium hydroxide solution (about 1.5 grams KOH in about 15 ml of 70% ethanol) was added to the mixture, and the mixture was refluxed for an additional 2 hours, diluted with about 225 ml of water, and acidified with about 25 ml of 2 N hydrochloric acid. The ethanol was evaporated and the solid product was filtered, dried, and recrystallized from glacial acidic acid to give white crystals.

EXAMPLE 12

In this example, a liquid crystalline compound within the scope of the present invention was made wherein a=1, $R_1$=CH$_2$=CH(CH$_2$)$_8$—, and $R_2$=—COOCH$_2$CH(CH$_3$)CH$_2$CH$_3$ in Formula 1. This compound, (S)-4-[(2-methyl-1-butoxy)carbonyl]phenyl 4-[4-(9'-decenyloxy)phenyl]benzoate, was made in accordance with the procedure of Example 1 with the following exceptions.

About 1.30 grams (3.7 mmol) of 4-[4-(9'-decenyloxy)phenyl]benzoic acid were used in Example 12 instead of the 7.1 grams of 4-[4-(allyloxy)phenyl]benzoic acid used in Example 1. Additionally, in Example 12, about 0.77 grams (3.7 mmol) of (S)-2-methyl-1-butyl 4-hydroxybenzoate were used in lieu of the 4-methoxyphenol used in Example 1. Methylene chloride and methanol were used to recrystallize the product of this example.

EXAMPLE 13

In this example, a liquid crystalline compound within the scope of the present invention may be made wherein a=2, $R_1$=CH$_2$=CH(CH$_2$)$_8$—, and $R_2$=—OCH$_3$ in Formula 1. This compound, 4'-methoxybiphenyl-4-yl 4-[4-(9'-decenyloxy)phenyl]benzoate, is made in accordance with the procedure of Example 1 with the following exceptions.

About 2.8 grams (8 mmol) of 4-[4-(9'-decenyloxy)phenyl]benzoic acid are used in Example 13 instead of the 7.1 grams of 4-[4-(allyloxy)phenyl]benzoic acid used in Example 1. Additionally, in Example 13, about 1.6 grams (8 mmol) of 4-methoxyphenol are used instead of the 3.4 grams of this compound used in Example 1. Ethanol may be used to recrystallize the product of this example.

The present invention also relates to novel liquid crystalline polymers which are formed by attaching the various liquid crystalline compounds of Formula 1 to a polysiloxane backbone. In particular, methylpolysiloxanes have exhibited good efficiency when used as the polymer backbones in Formula 2 and are presently preferable. Additionally, phenyl substitution of some of the methyl groups in such a methylpolysiloxane polymer backbone is also within the scope of the present invention. Further, it will be recognized that other polymers, such as carbon polymers, may be used as a polymer backbone, and that the polymers of the present invention are not limited to polysiloxane backbones. However, polysiloxane backbones are presently preferred for chromatographic applications.

The novel liquid crystalline polymers of the present invention have the following general formula:

FORMULA 2

In Formula 2 above, [CH$_2$]$_a$ and [CH$_2$]$_d$ correspond to R$_1$ in Formula 1 after R$_1$ has been attached to a silicon atom in a polysiloxane backbone. Thus, a and d are preferably integers from about 0 to about 22, and the [CH$_2$]$_a$ and [CH$_2$]$_d$ moieties of Formula 2 are from about 0 to about 22 carbons long. As with the liquid crystalline compounds of Formula 1, although carbon chain lengths greater than this might be used for [CH$_2$]$_a$ and [CH$_2$]$_d$ in Formula 2, it has been found that the chromatographic utility of the resultant polymers tends to be lost when larger carbon chain lengths are used. The most presently preferred values for a and d in Formula 2 are 3, 5, and 10.

The [CH$_2$]$_a$ and [CH$_2$]$_d$ moieties in the polymers of Formula 2 are typically referred to as spacer moieties, since they determine the distance between the polysiloxane backbone and the mesomorphic side chains represented by —O—(C$_6$H$_4$)$_2$—COO—(C$_6$H$_4$)$_b$—R$_1$ and —O—(C$_6$H$_4$)$_2$—COO—(C$_6$H$_4$)$_e$—R$_2$. Thus, by increasing the value of a and d as desired, the distance between the polysiloxane backbone and the mesomorphic side chains of the polymers of Formula 2 may be increased or decreased as desired. The efficiency, selectivity, thermal stability, and solubility of the resultant polymer are factors which should be considered in determining the optimum values for a and d in a given application.

Further, b and e in Formula 2 correspond to a in Formula 1. Thus, b and e are either 1 or 2, with b and e both being 1 in the most presently preferred embodiment. Although it is possible for b and e to be integers larger than 2, it is anticipated that the chromatographic utility of the resultant polymer may tend to disappear when the values of b and e are increased much greater than 2.

Similarly, $R_1$ and $R_2$ in Formula 2 correspond to $R_2$ in Formula 1. Thus, $R_1$ and $R_2$ in Formula 2 may be represented by virtually any group which will maintain the liquid crystalline properties of the resultant polymer. For example, $R_1$ and $R_2$ of Formula 2 may be represented by hydrogen, an alkyl group, an alkoxy group, a carboxy alkyl group, an aryl group, an arylalkyl group, an arylalkoxy group, a carboxy arylalkoxy group, a hydroxy group, a hydroxy alkyl group, a cyano group, a cyano alkyl group, an amino group, an amino alkyl group, an amido group, an amido alkyl group, or substitutions thereof.

Again, in order to preserve the liquid crystalline properties of the resultant polymer, it has been presently found preferable to maintain the main carbon chain length of $R_1$ and $R_2$ in Formula 2 at a length of 20 carbons or less. Although main carbon chain lengths greater than this are possible for $R_2$ and $R_1$ in Formula 2, it has been found that the liquid crystalline properties of the polymer tend to disappear with such increasing chain lengths.

In several presently preferred embodiments, one or both of $R_1$ and $R_2$ of Formula 2 are represented by an alkoxy group, a carboxy alkyl group, a carboxy arylalkoxy group, or a cyano group. For example, in such preferred embodiments, $R_1$ and/or $R_2$ may be —$OCH_3$, —$COOCH_2CH(CH_3)CH_2CH_3$, —$COO(C_6H_4)OCH_3$, or —CN. However, many other chemical groups may also be used to produce polymers with liquid crystalline properties which are within the scope of the present invention. Thus, the chemical groups set forth hereinabove for $R_1$ and $R_2$ in Formula 1 are merely illustrative, and should not be considered comprehensive.

Further in Formula 2, $R_3$ and $R_{10}$ may also be virtually any group which will maintain the liquid crystalline nature of the polymer. For example, $R_3$ and $R_{10}$ may be represented by hydrogen, lower alkyl, lower aryl, lower arylalkyl, lower silyl alkyl, and substitutions thereof. In one presently preferred embodiment of the present invention, $R_3$ and $R_{10}$ are both $Si(CH_3)_3$.

The other groups, $R_4$, $R_5$, $R_6$, $R_7$, $R_8$, and $R_9$ in Formula 2 above may again be virtually any groups which will maintain the liquid crystalline nature of the polymer. For example, $R_4$, $R_5$, $R_6$, $R_7$, $R_8$, and $R_9$ may be represented by hydrogen, lower alkyl, lower aryl, lower arylalkyl, other mesomorphic side chains having the general formula —$(CH_2)_a$—O—$(C_6H_4)_2$—COO—$(C_6H_4)_b$—$R_1$, or substitutions thereof. In one presently preferred embodiment of the present invention, $R_4$, $R_5$, $R_6$, $R_7$, $R_8$, and $R_9$ are all methyl groups (—$CH_3$).

As with the compounds of Formula 1, it will be recognized that substitutions of any of the foregoing chemical groups for $R_1$–$R_{10}$ in Formula 2 will be within the scope of the present invention. By way of example only, substituting a halogen in one of these chemical groups for a hydrogen will be considered to be within the scope of the present invention. Thus, all well-known chemical substitutions or derivatives of the polymers of Formula 2 are to be considered within the scope of the present invention where the liquid crystalline properties are preserved.

Further, c and f in Formula 2 determine the number of silicon-oxygen spacer units between mesomorphic side chains along the polysiloxane backbone. Thus, by varying c and f, the space between adjacent mesomorphic side chains may be increased or decreased as desired. In general, c and f are preferably integers from about 0 to about 10. Of course when c and/or f are 0, there are no spacer units between the corresponding adjacent mesomorphic side chains. In one presently preferred embodiment of the present invention, c and f are integers from about 0 to about 5, with values of 0, 1, and 2 being the most presently preferred. The selection of an appropriate value for c and f must ensure that the liquid crystalline properties of the polymer are not lost. The efficiency, selectivity, thermal stability, and solubility of the resultant polymer are factors which should be considered in determining the optimum values for c and f in a given application.

The number of mesomorphic side chains in the polymers of Formula 2 is determined by the value of g. In one presently preferred embodiment, g is an integer from about 1 to about 200. Although it is possible for g to be integers larger than 200, it has been found that the liquid crystalline polymers produced with g at greater values tend to have less than optimal efficiency and solubility.

In the presently most preferred embodiment, polymers made in accordance with Formula 2 have a g value within the range of about 1 to about 80, with the presently most preferred values for g being around 15–20. However, it will be appreciated that the precise value of g employed will depend upon the particular application involved, with the optimum value of g depending upon such factors as the efficiency and solubility of the resultant polymer.

One presently preferred procedure for preparing polymers in accordance with Formula 2 is given in Procedure II below.

Procedure II

In this procedure, poly[oxy(methylsilylene)] is reacted with an olefinic compound within the scope of Formula 1 wherein $R_1$ is represented by $CH_2$=$CH(CH_2)_b$—, with the reactants being combined with one vinyl molecule for each SiH in the polymer. To the mixture of these two reactants is added enough toluene to dissolve the reactants and a catalytic amount of chloroplatinic acid (about 0.1M) in 2-propanol. The resultant mixture is heated to a temperature within the range of about 75° C. to about 95° C. for a period of about 16 hours to about 24 hours until the reaction is completed.

The polymer thus produced is precipitated by adding an equal volume of methanol to the reaction mixture. The polymer product is then purified by dissolving it in a minimal amount of methylene chloride, and subsequently precipitating the polymer by adding an equal volume of methanol. This process may be repeated two or more times in order to obtain better purity. The purified product is then dried at a temperature within the range of about 30° C. to about 60° C. under a vacuum of about 0.1 torr to about 1 torr for a period of about 12 hours to about 24 hours.

The following examples are given to illustrate various polymers which have been made or may be made in accordance with Formula 2 of the present invention. These examples are given by way of example only, and it is to be understood that the following examples are not comprehensive of the many different polymers which can be made in accordance with the present invention.

EXAMPLE 14

In this example, a liquid crystalline polymer within the scope of the present invention was made wherein $a=3$, $b=1$, $c=0$, $d=3$, $e=1$, $f=0$, $g=$ about 17, $R_1=-OCH_3$, $R_2=-OCH_3$ $R_3=-Si(CH_3)_3$, $R_4=-CH_3$, $R_7=-CH_3$, and $R_{10}=-Si(CH_3)_3$ in Formula 2. This polymer was made in accordance with the following procedure.

About 0.25 grams of poly[oxy(methylsilylene)] (having about 4 mmol of SiH) and 1.5 grams (4 mmol) of the compound made in Example 1 were combined. About 2 ml of toluene and about 0.2 ml of a 0.1M solution of chloroplatinic acid in 2-propanol were added to the mixture, and the mixture was heated to about 80° C. for about 16 hours.

The polymer thus produced was precipitated by adding an equal volume of methanol to the reaction mixture. The polymer product was then purified by dissolving it in about 1 ml of methylene chloride, and subsequently precipitating the polymer by adding about 2 ml of methanol. This process was repeated two times. The purified product was then dried at about 80° C. under a vacuum of about 0.1 torr for about 24 hours.

In Example 14, the poly[oxy(methylsilylene)] used was polymethylhydrosiloxane purchased from Petrarch, Bristol, Pa., under Stock No. PS-120, and had an average molecular weight of 2270, about 50% SiH, and a viscosity of about 30 poise.

EXAMPLE 15

In this example, a liquid crystalline polymer within the scope of the present invention was made wherein $a=3$, $b=1$, $c=0$, $d=3$, $e=1$, $f=0$, $g=$ about 17, $R_1=-COOCH_2CH(CH_3)CH_2CH_3$, $R_2=-COOCH_2CH(CH_3)CH_2CH_3$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 74 mg (0.43 mmol) of the compound made in Example 2 were used in Example 15 instead of the 1.5 grams of the compound made in Example 1 which were used in Example 14. Also, about 10 mg of the polymethylhydrosiloxane (having about 0.42 mmol of SiH) were used in Example 15 instead of the 0.25 grams of this polymer used in Example 14.

EXAMPLE 16

In this example, a liquid crystalline polymer within the scope of the present invention was made wherein $a=3$, $b=1$, $c=0$, $d=3$, $e=1$, $f=0$, $g=$ about 17, $R_1=-CN$, $R_2=-CN$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 58 mg (1.65 mmol) of the compound made in Example 3 were used in Example 16 instead of the 1.5 grams of the compound made in Example 1 which were used in Example 14. Also, about 94.5 mg of the polymethylhydrosiloxane (having about 1.5 mmol of SiH) were used in Example 16 instead of the 0.25 grams of this polymer used in Example 14.

EXAMPLE 17

In this example, a liquid crystalline polymer within the scope of the present invention was made wherein $a=3$, $b=2$, $c=0$, $d=3$, $e=2$, $f=0$, $g=$ about 17, $R_1=-COOCH_2CH(CH_3)CH_2CH_3$, $R_2=-COOCH_2CH(CH_3)CH_2CH_3$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 87 mg (0.43 mmol) of the compound made in Example 6 were used in Example 17 instead of the 1.5 grams of the compound made in Example 1 which were used in Example 14. Also, about 10 mg of the polymethylhydrosiloxane (having about 0.42 mmol of SiH) were used in Example 17 instead of the 0.25 grams of this polymer used in Example 14.

EXAMPLE 18

In this example, a liquid crystalline polymer within the scope of the present invention was made wherein $a=5$, $b=1$, $c=0$, $d=5$, $e=1$, $f=0$, $g=$ about 17, $R_1=-OCH_3$, $R_2=-OCH_3$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 65 mg (0.43 mmol) of the compound made in Example 7 were used in Example 18 instead of the 1.5 grams of the compound made in Example 1 which were used in Example 14. Also, about 10 mg of the polymethylhydrosiloxane (having about 0.42 mmol of SiH) were used in Example 18 instead of the 0.25 grams of this polymer used in Example 14.

EXAMPLE 19

In this example, a liquid crystalline polymer within the scope of the present invention was made wherein $a=5$, $b=1$, $c=0$, $d=5$, $e=1$, $f=0$, $g=$ about 17, $R_1=-COOCH_2CH(CH_3)CH_2CH_3$, $R_2=-COOCH_2CH(CH_3)CH_2CH_3$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 79 mg (0.43 mmol) of the compound made in Example 8 were used in Example 19 instead of the 1.5 grams of the compound made in Example 1 which were used in Example 14. Also, about 10 mg of the polymethylhydrosiloxane (having about 0.42 mmol of SiH) were used in Example 19 instead of the 0.25 grams of this polymer used in Example 14.

EXAMPLE 20

In this example, a liquid crystalline polymer within the scope of the present invention was made wherein $a=5$, $b=2$, $c=0$, $d=5$, $e=2$, $f=0$, $g=$ about 17, $R_1=-COOCH_2CH(CH_3)CH_2CH_3$, $R_2=-COOCH_2CH(CH_3)CH_2CH_3$, $R_3=-Si(CH_3)_3$, $R_4=-CH_3$, $R_7=-CH_3$, and $R_{10}=-Si(CH_3)_3$ in Formula 2. This polymer was made in accordance with the procedure of Example 14 with the following exceptions. About 92 mg (0.43 mmol) of the compound made in Example 10 were used in Example 20 instead of the 1.5 grams of the compound made in Example 1 which were used in Example 14. Also, about 10 mg of the polymethylhydrosiloxane (having about 0.42 mmol of SiH) were used in Example 20 instead of the 0.25 grams of this polymer used in Example 14.

EXAMPLE 21

In this example, a liquid crystalline polymer within the scope of the present invention was made wherein $a=10$, $b=1$, $c=$ an average of about 1, $d=10$, $e=1$, f=an average of about 1, g=about 80, $R_1$=—OCH$_3$, $R_2$=—OCH$_3$, $R_3$=—Si(CH$_3$)$_3$, $R_4$=—CH$_3$, $R_5$=—CH$_3$, $R_6$=—CH$_3$, $R_7$=—CH$_3$, $R_8$=—CH$_3$, $R_9$=—CH$_3$, and $R_{10}$=—Si(CH$_3$)$_3$ in Formula 2. This polymer was made in accordance with the procedure of Example 14 with the following exceptions. About 1 gram (2.18 mmol) of the compound made in Example 11 were used in Example 21 instead of the 1.5 grams of the compound made in Example 1 which were used in Example 14. Additionally, about 268 mg (having about 2 mmol of SiH) of a (50%) methylhydro-(50%)dimethylsiloxane copolymer (containing about 25% SiH) were used instead of the 0.25 grams of polymethylhydrosiloxane used in Example 14.

The (50%)methylhydro-(50%)dimethylsiloxane copolymer used in Example 21 was prepared in accordance with the following procedure. About 2.5 ml of acetonitrile and about 2.5 ml of water were added to about 0.033 mol of methyldiethoxysilane and about 0.033 mol of dimethyldimethoxysilane, and the resulting mixture was stirred for about one hour. A solution of benzenesulfonic acid (about 0.1M in H$_2$O) was added and the mixture was stirred under an argon purge for about 26 hours. An excess of hexamethyldisilazane was added and the solution was stirred at about 20° C. for about 15 minutes. The temperature was then raised to about 80° C. for about two hours to remove the residual disilazane. The endcapped polymer was dissolved in methylene chloride and precipitated with twice the volume of methanol. The fractionation process was repeated twice, and the dissolved polymer was filtered through a millipore filter. A colorless viscous oil remained after solvent evaporation.

EXAMPLE 22

In this example, a liquid crystalline polymer within the scope of the present invention was made wherein a=3, b=1, c=0, d=5, e=1, f=0, g=about 17, $R_1$=—OCH$_3$, $R_2$=—OCH$_3$, $R_3$=—Si(CH$_3$)$_3$, $R_4$=—CH$_3$, $R_7$=—CH$_3$, and $R_{10}$=—Si(CH$_3$)$_3$ in Formula 2. This polymer was made in accordance with the procedure of Example 14 with the following exceptions. About 72 mg (2 mmol) of the compound made in Example 1 and about 78 mg (2 mmol) of the compound made in Example 7 were used in Example 22 instead of the 1.5 grams of the compound made in Example 1 which were used in Example 14.

EXAMPLE 23

In this example, a liquid crystalline polymer within the scope of the present invention may be made wherein a=3, b=1, c=0, d=5, e=1, f=0, g=about 17, $R_1$=—COOCH$_2$CH(CH$_3$)CH$_2$CH$_3$, $R_2$=—COOCH$_2$CH(CH$_3$)CH$_2$CH$_3$, $R_3$=—Si(CH$_3$)$_3$, $R_4$=—CH$_3$, $R_7$=—CH$_3$, and $R_{10}$=—Si(CH$_3$)$_3$ in Formula 2. This polymer may be made in accordance with the procedure of Example 14 with the following exceptions. About 40 mg (0.22 mmol) of the compound made in Example 2 and about 43 mg (0.22 mmol) of the compound made in Example 8 are used in Example 23 instead of the 1.5 grams of the compound made in Example 1 which were used in Example 14.

EXAMPLE 24

In this example, a liquid crystalline polymer within the scope of the present invention was made wherein a=3, b=1, c=an average of about 1, d=10, e=1, f=an average of about 1, g=about 80, $R_1$=—OCH$_3$, $R_2$=—OCH$_3$, $R_3$=—Si(CH$_3$)$_3$, $R_4$=—CH$_3$, $R_5$=—CH$_3$, $R_6$=—CH$_3$, $R_7$=—CH$_3$, $R_8$=—CH$_3$, $R_9$=—CH$_3$, and $R_{10}$=—Si(CH$_3$)$_3$ in Formula 2. This polymer was made in accordance with the procedure of Example 21 with the following exceptions. About 180 mg (0.5 mmol) of the compound made in Example 1 and about 229 mg (0.5 mmol) of the compound made in Example 11 were used in Example 24 instead of the 1 gram of the compound made in Example 11 which was used in Example 21. Also, about 122 mg (containing about 0.91 mmol of SiH) of the (50%)methylhydro-(50%)dimethylsiloxane copolymer were used in Example 25 instead of the 268 mg of this polymer used in Example 21.

EXAMPLE 25

In this example, a liquid crystalline polymer within the scope of the present invention was made wherein a=3, b=1, c=an average of about 1, d=10, e=1, f=an average of about 1, g=about 80, $R_1$=—COOCH$_2$CH(CH$_3$)CH$_2$CH$_3$, $R_2$=—COOCH$_2$CH(CH$_3$)CH$_2$CH$_3$, $R_3$=—Si(CH$_3$)$_3$, $R_4$=—CH$_3$, $R_5$=—CH$_3$, $R_6$=—CH$_3$, $R_7$=—CH$_3$, $R_8$=—CH$_3$, $R_9$=—CH$_3$, and $R_{10}$=—Si(CH$_3$)$_3$ in Formula 2. This polymer was made in accordance with the procedure of Example 21 with the following exceptions. About 178 mg (0.4 mmol) of the compound made in Example 2 and about 217 mg (0.4 mmol) of the compound made in Example 12 were used in Example 25 instead of the 1 gram of the compound made in Example 11 which was used in Example 21. Also, about 98 mg (containing about 0.73 mmol of SiH) of the (50%)methylhydro-(50%)dimethylsiloxane copolymer were used in Example 25 instead of the 268 mg of this polymer used in Example 21.

The compounds and polymers of the present invention have shown utility in connection with stationary phases used in gas-liquid chromatography. The transition phase temperatures measured for some of the compounds and polymers made in the foregoing examples are given in Table I below.

TABLE I

| Example No. | Phase Transition Temperatures/°C. |
|---|---|
| 1 | k 137 n 243 i |
| 2 | k 118 s 198 n* 213 i |
| 3 | k 160 n 249 i |
| 4 | k 158 s 210 n > 350 i |
| 5 | k 214 n 290 i |
| 6 | k 152 s 240 n* 278 i |
| 7 | k 133 s 172 n 253 i |
| 8 | k 105 s 198 i |
| 10 | k 135 s 295 n* 315 i |
| 11 | k 88 s 158 n 187 i |
| 12 | k 46 s 168 i |
| 14 | g 104 s 308 i |
| 15 | g 190 s 235 n* 248 i |
| 16 | g 105 s 175 s' > 350 i |
| 17 | g 149 s 254 n* 291 i |
| 18 | g 109 s 295 i |
| 19 | g 113 s 200 i |
| 20 | g 114 s 350 d |
| 21 | g 92 s 246 n 286 i |
| 22 | g 120 s 297 i |
| 24 | g 60 s 226 i |

TABLE I-continued

| Example No. | Phase Transition Temperatures/°C. |
|---|---|
| 25 | g 182 s 225 i | k = crystalline
g = glassy
s = smectic
s' = smectic, (less ordered)
n = nematic
n* = cholesteric
i = isotropic
d = decomposition The various phases and transition temperatures which were found for the compounds and polymers produced in the foregoing examples may be found in Table I by reading from left to right. For example, the polymer produced in Example 14 was in a glassy phase up to about 104° C., in a smectic phase from about 104° C.–308° C., and in an isotropic phase above about 308° C. The polymer produced in Example 18 was in a glassy phase up to about 109° C., in a smectic phase from about 109° C.–295° C., and in an isotropic phase above about 295° C. Thus, these polymers have smectic phases over a relatively wide range of temperatures.

As noted from Table 1, the phase transition temperature ranges are generally widened once the mesomorphic compounds are secured to the polysiloxane polymer backbone. Such widening of the smectic phase temperature regions yields polymers which have utility as stationary phases in chromatographic columns.

One presently preferred procedure for applying the polymers of the present invention to a chromatographic column is given in Procedure III below.

Procedure III

In this procedure, the polymer to serve as the stationary phase is statically coated to fused silica capillary columns. The fused silica capillaries (for example, about 10–30 meters long and about 50–500 micrometers in inner diameter) are prepared for chromatographic analysis in accordance with the present invention as follows.

First, the fused silica capillaries are purged with dry nitrogen gas at about 250° C. for about two hours before use. The polymer is dissolved in methylene chloride at about 35° C. at a sufficient concentration to provide a film thickness of about 0.05–0.50 micrometers by the static coating method. Before filling the fused silica capillaries, the coating solution is carefully filtered through a two-micrometer metal filter device. The columns are then coated with the polymer and the columns are purged with nitrogen gas for about 30 minutes to remove all traces of solvent. The coating or stationary phase thus applied to the fused silica capillaries is next preferably cross-linked using azo-t-butane as free radical initiator.

To achieve such cross-linking, the coated columns are purged with azo-t-butane saturated nitrogen gas. The column ends are then sealed, and the columns are heated from about 40° C. to about 220° C. by increasing the temperature at the rate of about 4° C. per minute, and holding at the final temperature of about 220° C. for about 30–40 minutes. After cross-linking, the column is purged with dry nitrogen gas at room temperature to remove excess azo-t-butane and reaction by-products. Such a cross-linking procedure provides cross-linkages between the methyl and/or methylene functional groups in the polymer. Of course, it will be recognized that other free radical initiators can be used instead of azo-t-butane and that the cross-linking reaction can be performed statically in a sealed column as set forth in this procedure, or dynamically where the column is purged with an inert gas during the reaction.

EXAMPLE 26

In this example, the liquid crystalline polymer of Example 14 was applied as a stationary phase in a gas-liquid chromatographic column. In this example, an untreated fused silica capillary column, about 20 meters long and about 0.2 millimeters in inner diameter (supplied by Hewlett-Packard, Avondale, Pa.), was statically coated with about a 0.15 micrometer film of the polymer of Example 14.

The fused silica capillary was first purged with dry nitrogen gas at about 250° C. for about two hours before use. About 12 mg of the polymer of Example 14 was then dissolved in about 5 ml of methylene chloride at about 35° C. Before filling the fused silica capillary, the polymer-containing solution was carefully filtered through a two-micrometer metal filter device. The capillary column was then coated with the polymeric solution to provide a film thickness of about 0.15 micrometers on the inside of the capillary column. The column was then purged with nitrogen gas for about 30 minutes to remove all traces of solvent.

The polymer of Example 14, thus applied to the fused silica capillary, was next cross-linked using azo-t-butane. To achieve this, the polymer-coated column was purged with azo-t-butane saturated nitrogen gas. The column ends were then sealed, and the column was heated from about 40° C. to about 220° C. by increasing the temperature at a rate of about 4° C. per minute, and holding at the final temperature of about 220° C. for about 30–40 minutes. After the cross-linking procedure was completed, the capillary column was purged with dry nitrogen gas at room temperature to remove excess azo-t-butane and reaction by-products. Advantageously, the cross-linked polymer thus produced exhibited the following transition phase temperatures: g 30 s>300 i.

EXAMPLES 27–33

In Examples 27, 28, 29, 30, 31, 32, and 33, the liquid crystalline polymers of Examples 16, 18, 20, 21, 22, 24, and 25, respectively, were applied as a stationary phase to a gas-liquid chromatographic column in accordance with the procedure of Example 26.

Cross-linking of the polymeric stationary phase has several advantages. First, cross-linking the polymeric stationary phase within the column helps to prevent washout of the polymer after repeated use. Further, as seen, for example, where the polymer of Example 14 is used as a stationary phase in Example 26, the smectic phase transition temperatures shown in Table I are widened to the following temperature range by cross-linking: g 30 s>300 i. Thus, cross-linking stabilizes the stationary phase and widens the temperature range of the smectic phase of the polymer used as the stationary phase.

Additionally, the stationary phases of the present invention can be used in supercritical fluid chromatography where even higher demands are put on the cross-linked polymers. Such cross-linked polymers have been found to withstand the strong solubilizing properties of supercritical fluids. Thus, the present invention has found particular utility in supercritical fluid chromatography applications.

The polymers of each of Examples 14, 15, 16, 18, 20, 21, 22, 24, and 25 have been chromatographically tested and have shown utility in separating various PAH compounds. For example, the following closely related structural isomers have been successfully separated using the polymers of the present invention: (1) hydroxydibenzothiophene isomers; (2) dibenzo[b,g]phenanthrene, dibenzo[c,g]phenanthrene, dibenz[a,c]anthracene, dibenz[a,h]anthracene, dibenz[a,j]anthracene, benzo[b]chrysene, benzo[c]chrysene, benzo[g]chrysene, benzo[a]naphthacene, pentaphene, pentacene, and picene; (3) aminophenanthrene isomers; (4) methylphenanthrene isomers; (5) methylchrysene isomers; (6) methylcarbazole isomers; (7) benz[a]anthracene, benzo[c]phenanthrene, chrysene, triphenylene, and naphthacene; (8) dimethyldibenzothiophene isomers; and (9) methylbenz[a]anthracene isomers.

In the drawings of the present application, several gas-liquid chromatograms are illustrated showing the exceptional separation achieved when the polymers of the present invention are used as stationary phases. In each of the gas-liquid chromatograms illustrated in the drawings, a Hewlett-Packard model 5880 gas chromotagraph equipped with a flame ionization detector and a flame photometric detector was used. Hydrogen gas at 50–100 cm s$^{-1}$ was used as the carrier gas.

Figure 1:
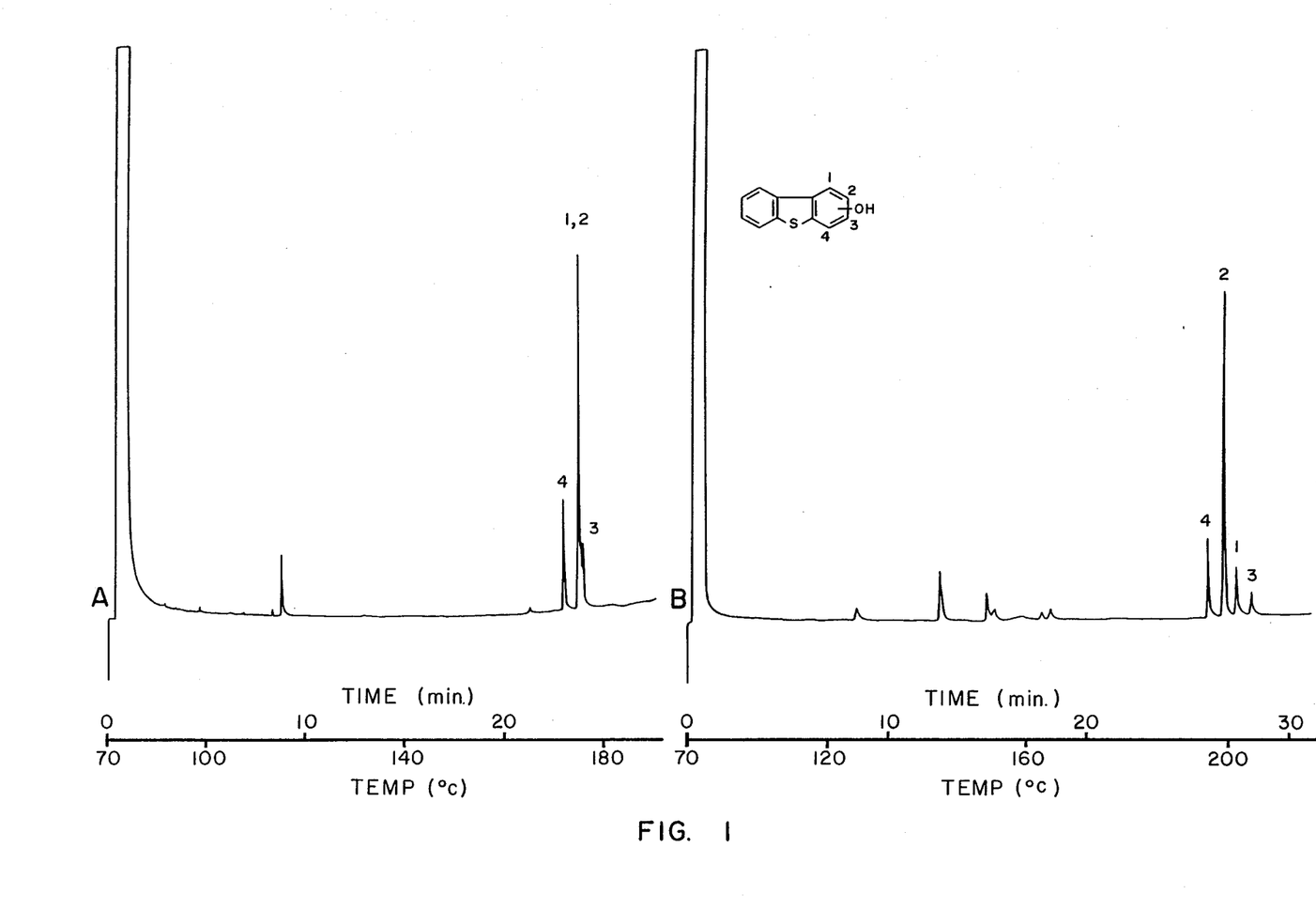
FIG. 1 illustrates two chromatograms wherein hydroxydibenzothiophene isomers were separated. Chromatogram A represents a prior art stationary phase, while chromatogram B represents a stationary phase made in accordance with the present invention.
Figure 2:
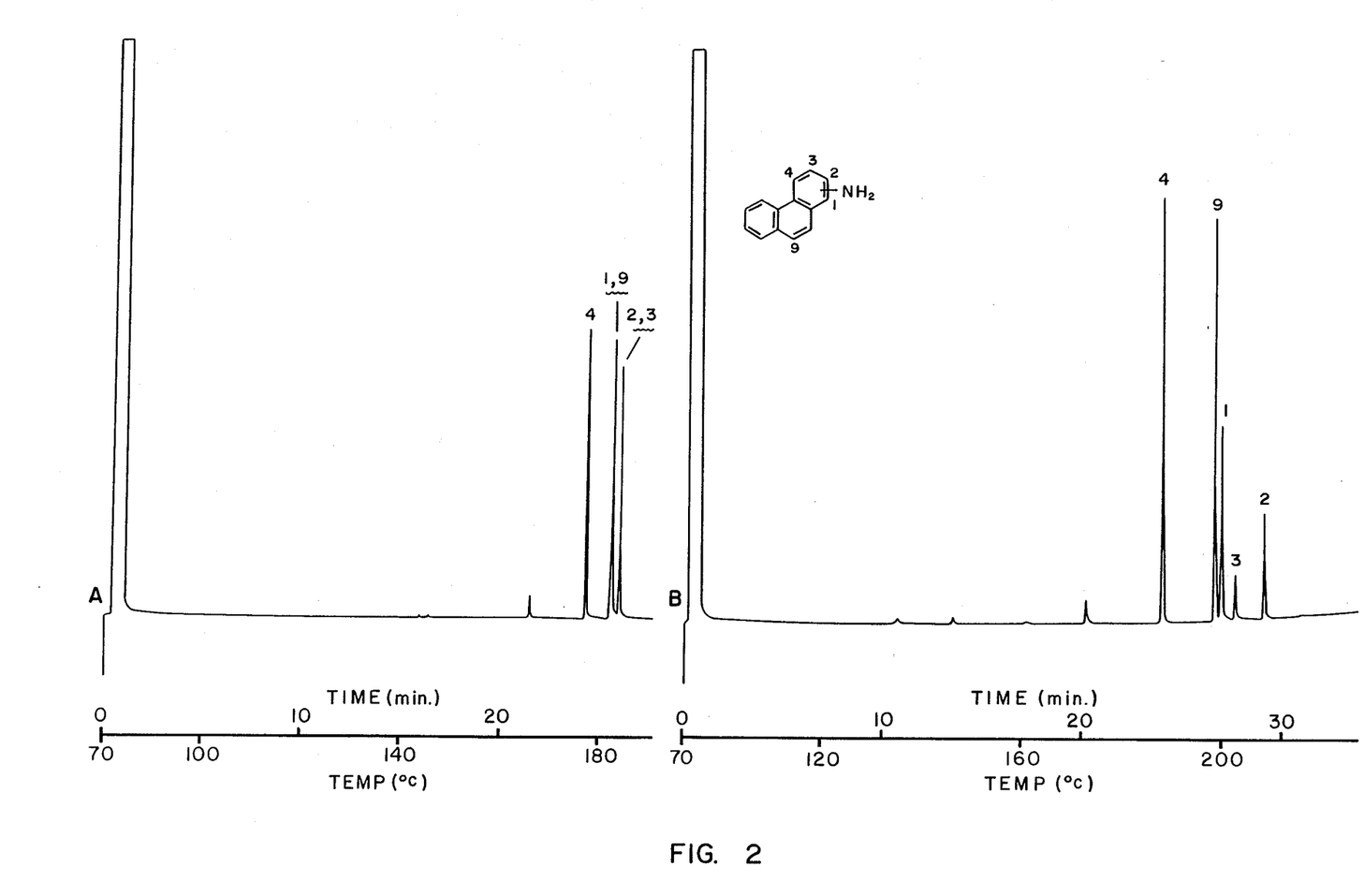
FIG. 2 illustrates two chromatograms wherein aminophenanthrene isomers were separated. Chromatogram A represents a prior art stationary phase, while chromatogram B represents a stationary phase made in accordance with the present invention.
Figure 3:
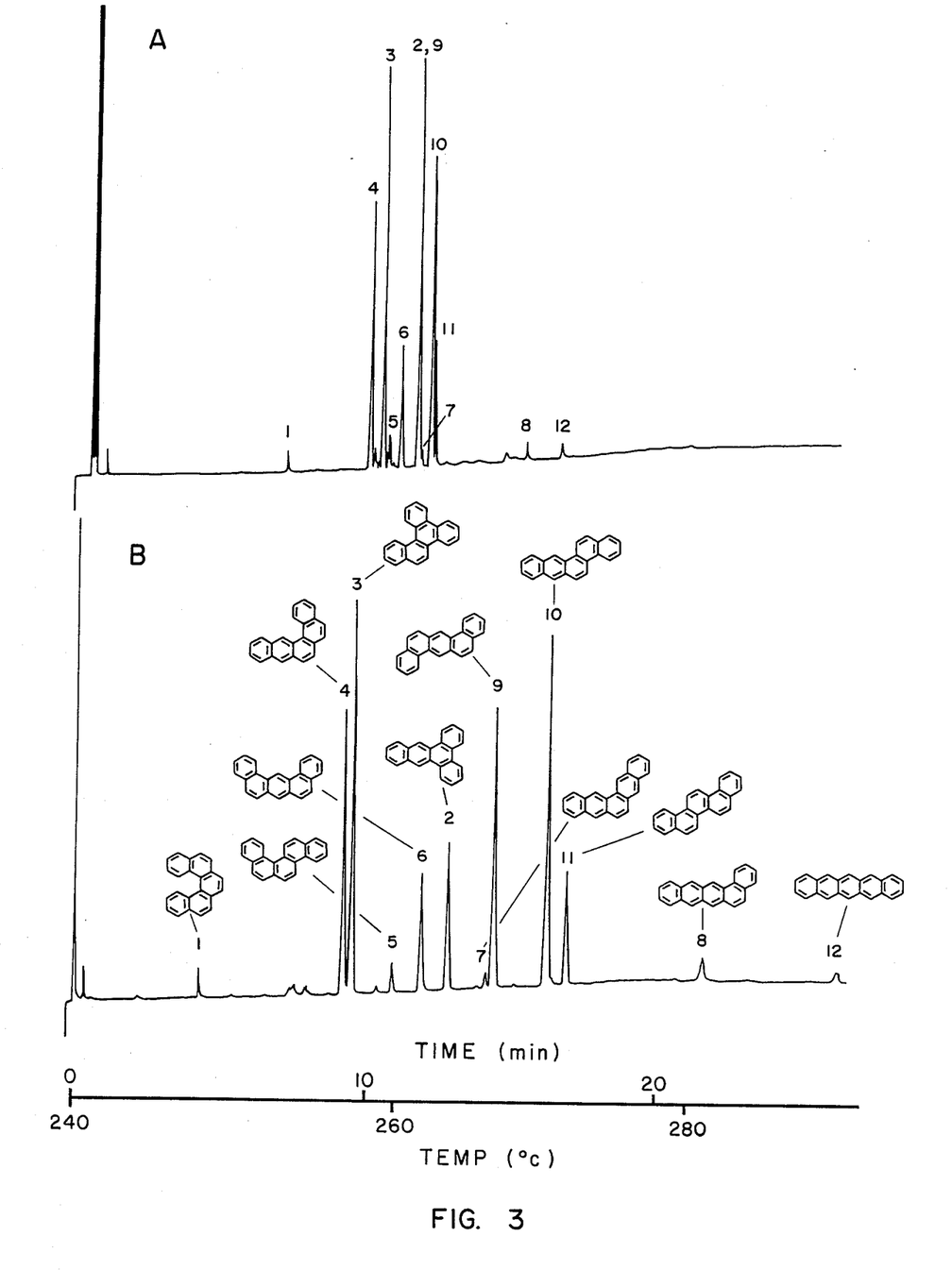
FIG. 3 illustrates two chromatograms wherein five-ring polycyclic aromatic isomers were separated. Chromatogram A represents a prior art stationary phase, while chromatogram B represents a stationary phase made in accordance with the present invention.

FIGS. 1, 2, and 3 show chromatograms wherein hydroxydibenzothiophene isomers, aminophenanthrene isomers, and various five-ring polycyclic aromatic hydrocarbon isomers, respectively, were separated in a gas chromatograph employing the stationary phase made in Example 31. In each of FIGS. 1, 2, and 3, chromatogram A represents the chromatographic separation achieved using a prior art stationary phase which is commonly known as SE-54, and chromatogram B represents the liquid crystalline polymer of Example 31. As seen in FIGS. 1, 2, and 3, the separation of the various PAH compounds was much better when using the polymer of Example 31 than that achieved using the prior art polymer.

Figure 4:
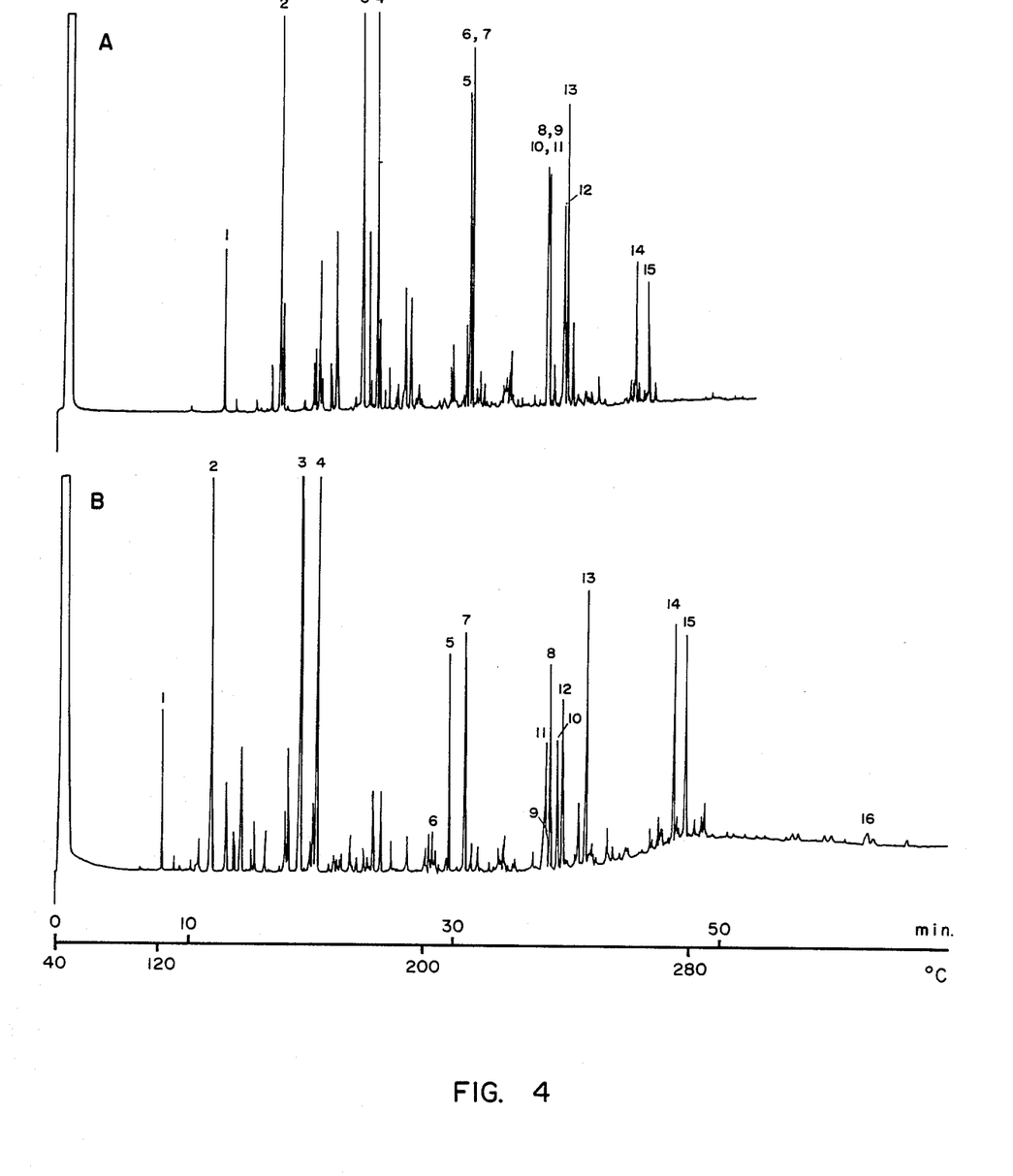
FIG. 4 illustrates two chromatograms wherein the various components of coal tar were separated. Chromatogram A represents a prior art stationary phase, while chromatogram B represents a stationary phase made in accordance with the present invention.

Similarly, FIG. 4 illustrates the chromatograms obtained when a sample of coal tar was passed through the gas chromatograph, with chromatogram A representing the SE-54 stationary phase and chromatograph B representing the polymer of Example 31. The peak identifications in chromatograms A and B of FIG. 4 are as follows: (1) fluorene, (2) phenanthrene, (3) fluoranthene, (4) pyrene, (5) benz[a]anthracene, (6) triphenylene, (7) chrysene, (8) benzo[a]fluoranthene, (9) benzo[b]fluoranthene, (10) benzo[k]fluoranthene, (11) benzo[j]fluoranthene, (12) benzo[e]pyrene, (13) benzo[a]pyrene, (14) indeno[1,2,3-cd]pyrene, (15) benzo[ghi]perylene, and (16) coronene.

From the foregoing, it will be appreciated that the polymers of the present invention provide stationary phases which achieve chromatographic separation of PAH compounds heretofore not possible, and also achieve better separation of PAH compounds analyzed in the prior art. Furthermore, the smectic phases of the polymers of the present invention provide good selectively and good efficiency, and therefore good separation of PAH compounds. Moreover, the polymers of the present invention have utility over a wide temperature range in the smectic phase.

When using the liquid crystalline compounds of the present invention alone (without the polymer backbone) in a chromatographic separation, the compounds are coated (bonded or unbonded) on a packing material for gas, supercritical, or liquid chromatography and packed into a column through which the sample to be analyzed is passed. Thus, the liquid crystalline compounds themselves, without the polymer backbone, may also be used to achieve chromatographic separation. However, it should be understood that the presently most preferred method for achieving chromatographic separation in accordance with the present invention is to use the liquid crystalline compounds attached to a polymer backbone.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for achieving chromatographic separation of polycyclic aromatic hydrocarbons, comprising the steps of:

preparing a compound of the formula:

wherein a is an integer from about 0 to about 22;
wherein b is 1 or 2;
wherein c is an integer from about 0 to about 10;
wherein d is an integer from about 0 to about 22;
wherein e is 1 or 2;
wherein f is an integer from about 0 to about 10;
wherein g is an integer from about 1 to about 200;
wherein $R_1$ and $R_2$ are selected from the group consisting of hydrogen, alkyl, alkoxy, carboxy alkyl, aryl, arylalkyl, arylalkoxy, carboxy arylalkoxy, hydroxy, hydroxy alkyl, cyano, cyano alkyl, amino, amino alkyl, amido, amido alkyl, and substitutions thereof, and wherein $R_1$ and $R_2$ each have from about 0 to about 20 carbons in the main carbon chain;
wherein $R_3$ and $R_{10}$ are selected from the group consisting of hydrogen, lower alkyl, lower aryl, lower arylalkyl, lower silyl alkyl, and substitutions thereof; and
wherein $R_4$, $R_5$, $R_6$, $R_7$, $R_8$, and $R_9$ are hydrogen, lower alkyl, lower aryl, lower arylalkyl, —(CH$_2$)$_a$—O—(C$_6$H$_4$)$_2$—COO—(C$_6$H$_4$)$_b$—R$_1$, or substitutions thereof;
applying said compound around the inside of a chromatography column;

passing a sample comprising a mixture of polycyclic aromatic hydrocarbons through the column so as to separate the mixture into its various polycyclic aromatic hydrocarbon components; and detecting and identifying the various polycyclic aromatic hydrocarbon components after their separation within the column.

2. A method as defined in claim 1 wherein said compound applied to said chromatography column is cross-linked.

3. A method as defined in claim 2 wherein said compound is cross-linked by passing azo-t-butane through said column.

4. A method as defined in claim 1 wherein the column is heated to a temperature within the range of from about 30° C. to about 300° C.

5. A method as defined in claim 1 wherein the polycyclic aromatic hydrocarbons in the sample are hydroxydibenzothiophene isomers.

6. A method as defined in claim 1 wherein the polycyclic aromatic hydrocarbons in the sample are selected from the group consisting of dibenzo[b,g]phenanthrene, dibenzo[c,g]phenanthrene, dibenz[a,c]anthracene, dibenz[a,h]anthracene, dibenz[a,j]anthracene, benzo[b]chrysene, benzo[c]chrysene, benzo[g]chrysene, benzo[a]naphthacene, pentaphene, pentacene, and picene.

7. A method as defined in claim 1 wherein the polycyclic aromatic hydrocarbons in the sample are aminophenanthrene isomers.

8. A method as defined in claim 1 wherein the polycyclic aromatic hydrocarbons in the sample are methylphenanthrene isomers.

9. A method as defined in claim 1 wherein the polycyclic aromatic hydrocarbons in the sample are methylchrysene isomers.

10. A method as defined in claim 1 wherein the polycyclic aromatic hydrocarbons in the sample are methylcarbazole isomers.

11. A method as defined in claim 1 wherein the polycyclic aromatic hydrocarbons in the sample are selected from the group consisting of benz[a]anthracene, benzo[c]phenanthrene, chrysene, triphenylene, and naphthacene.

12. A method as defined in claim 1 wherein the polycyclic aromatic hydrocarbons in the sample are dimethyldibenzothiophene isomers.

13. A method as defined in claim 1 wherein the polycyclic aromatic hydrocarbons in the sample are methylbenz[a]anthracene isomers.

* * * * *